(12) United States Patent
Osmundsen et al.

(10) Patent No.: US 11,780,798 B2
(45) Date of Patent: Oct. 10, 2023

(54) METHOD AND A SYSTEM FOR PRODUCING GLYCOLIC ACID AND/OR GLYCOLATE

(71) Applicant: HALDOR TOPSØE A/S, Kgs. Lyngby (DK)

(72) Inventors: Christian Mårup Osmundsen, Gentofte (DK); Esben Taarning, Frederiksberg (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 16/461,989

(22) PCT Filed: Nov. 22, 2017

(86) PCT No.: PCT/EP2017/080065
§ 371 (c)(1),
(2) Date: May 17, 2019

(87) PCT Pub. No.: WO2018/095973
PCT Pub. Date: May 31, 2018

(65) Prior Publication Data
US 2019/0284122 A1 Sep. 19, 2019

(30) Foreign Application Priority Data
Nov. 24, 2016 (DK) .......................... PA 2016 00728

(51) Int. Cl.
| | | |
|---|---|---|
| *C07C 51/235* | (2006.01) |
| *B01J 23/44* | (2006.01) |
| *B01J 23/52* | (2006.01) |
| *C07C 45/60* | (2006.01) |
| *C07C 51/285* | (2006.01) |
| *C07C 59/06* | (2006.01) |
| *C07C 27/00* | (2006.01) |

(52) U.S. Cl.
CPC ............. *C07C 51/235* (2013.01); *B01J 23/44* (2013.01); *B01J 23/52* (2013.01); *C07C 27/00* (2013.01); *C07C 45/60* (2013.01); *C07C 51/285* (2013.01); *C07C 59/06* (2013.01)

(58) Field of Classification Search
CPC ....... C07C 51/235; C07C 27/00; C07C 45/60; C07C 51/285; C07C 59/06; B01J 23/44; B01J 23/52
See application file for complete search history.

(56) References Cited

U.S. PATENT DOCUMENTS

| | | | |
|---|---|---|---|
| 4,382,148 A * | 5/1983 | Drent .................... | C07C 29/141 |
| | | | 568/458 |
| 5,397,582 A | 3/1995 | Underwood et al. | |
| 7,094,932 B2 * | 8/2006 | Majerski ................ | C07C 45/00 |
| | | | 426/103 |
| 7,122,698 B2 | 10/2006 | Yoshida et al. | |
| 8,329,613 B2 * | 12/2012 | Begli ....................... | B01J 23/52 |
| | | | 502/344 |
| 10,570,078 B2 * | 2/2020 | Larsen .................... | C07C 27/04 |
| 11,034,713 B2 * | 6/2021 | Shunmugavel ...... | B01J 29/7057 |
| 2004/0022912 A1 | 2/2004 | Majerski et al. | |
| 2010/0022740 A1 * | 1/2010 | Okazaki ................. | C07C 59/06 |
| | | | 528/271 |
| 2013/0281733 A1 * | 10/2013 | Han ........................ | C07C 45/60 |
| | | | 562/515 |
| 2017/0129913 A1 * | 5/2017 | Shunmugavel ...... | B01J 29/7057 |
| 2017/0197893 A1 * | 7/2017 | Marup .................. | C07C 29/145 |
| 2019/0119187 A1 * | 4/2019 | Larsen ...................... | B01J 8/26 |
| 2022/0306563 A1 * | 9/2022 | Yan ......................... | B01J 21/18 |

FOREIGN PATENT DOCUMENTS

| | | | | |
|---|---|---|---|---|
| JP | S5346916 A * | 4/1978 | ............. | B01J 23/00 |
| JP | S5346916 A | 4/1978 | | |
| JP | S53-98923 A | 8/1978 | | |
| JP | S6010016 B2 | 3/1985 | | |
| JP | 6039063 B2 | 9/1985 | | |
| JP | H8-92155 A | 4/1996 | | |
| JP | 2005-330225 A | 12/2005 | | |
| JP | 2006117576 A | 5/2006 | | |
| JP | 2008-31081 A | 2/2008 | | |
| JP | 2013-1696 A | 1/2013 | | |
| JP | 2017-519792 A | 7/2017 | | |
| JP | 2017-519793 A | 7/2017 | | |
| WO | WO-2015193461 A2 * | 12/2015 | ............. | A23L 27/34 |
| WO | 2016/001136 A | 1/2016 | | |

(Continued)

OTHER PUBLICATIONS

Gil et al., 2011, Chem. Eng. J. 178 (2011) 423-435. (Year: 2011).*

(Continued)

*Primary Examiner* — Alexander R Pagano
(74) *Attorney, Agent, or Firm* — Boone IP Law

(57) ABSTRACT

A method and a system for producing glycolic acid and/or glycolate from sustainable resources. A method for catalytic production of glycolic acid and/or glycolate including the step of: oxidation of a starting material including between 0.1-100 wt/wt % glycolaldehyde at a temperature of between −10° C. and 100° C. with an oxidant in the presence of a metal-based catalyst including a catalytically active metal, which is selected from the group of palladium and platinum; or mixtures thereof.

19 Claims, No Drawings

(56) References Cited

FOREIGN PATENT DOCUMENTS

WO  2016/001169 A1  1/2016

OTHER PUBLICATIONS

T. Mallat et al., 19 Catalysts Today, 247-284 (1994) (Year: 1994).*
M. Baumann et al., Beilstein Journal of Organic Chemistry, 1194-1219 (2015) (Year: 2015).*
R. Anderson et al., 345 Adv. Synth. Catal. 517-523 (2003) (Year: 2003).*
J. Piskorz et al., 9 Journal of Analytical and Applied Pyrolysis, 121-137 (1986) (Year: 1986).*
R. de Lima et al., 709 Journal of Electroanalytical Chemistry, 77-82 (2013) (Year: 2013).*
F. Fulop et al., Practicals of Organic Chemistry (2015) (Year: 2015).*
S. Biella et al., 197 Journal of Molecular Catalyst A: Chemical, 207-221 (2003) (Year: 2003).*
J. Hodge et al., 1 Agricultural and Food Chemistry, 928-943 (1953) (Year: 1953).*
International Search Report (with English translation) and Written Opinion issued in corresponding International Patent Application No. PCT/EP2017/080065, 14 pages (dated Jan. 24, 2018).
Shibata, M., et al., "Selective Oxidation of the Aldehyde Functional Group in the Glycolaldehyde Molecule at Pt Electrodes Modified by AD-Atoms," Electrochimica Acta, Elsevier Science Ltd., Great Britain, vol. 39, No. 11/12, pp. 1877-1880 (1994).
Unknown, "Database WPI Week 197823", Thompsons Scientific, London Great Britain, AN 1978-41241A XP002777587 (JPS5346916A Kawaken Fine Chem Co, JPS6010016B2 Kawaken Fine Chem Co), 2 pages, (2017).
Vitasari, C., et al., "Laboratory scale conceptual process development for the isolation of renewable glycolaldehyde from pyrolysis oil to produce fermentation feedstock", Green Chemistry 14, 321 (2012).
Office Action (The First Office Action) dated Jun. 2, 2021 by the China National Intellectual Property Administration in corresponding Chinese Patent Application No. 2017800711306, and an English Translation of the Office Action. (15 pages).
Office Action (Notice of Reasons for Refusal) dated Jun. 9, 2021, by the Japanese Patent Office in corresponding Japanese Patent Application No. 2019-527870, and an English Translation of the Office Action. (13 pages).
Office Action (Notice of Grounds for Preliminary Rejection) dated Dec. 28, 2022, by the Intellectual Property Office in corresponding Korean Patent Application No. 10-2019-7012914, and an English Translation of the Office Action. (6 pages).

\* cited by examiner

METHOD AND A SYSTEM FOR PRODUCING GLYCOLIC ACID AND/OR GLYCOLATE

FIELD

Disclosed herein is a method and a product obtainable by the method, and a system for producing glycolic acid and/or glycolate.

BACKGROUND

Glycolic acid may be produced by reacting formaldehyde, carbon monoxide and water. This process requires the use of strong acid catalysts (such as HF, $H_2SO_4$ or HCl), intermediate temperatures (between 50-100° C.) and very high pressures (between 100-500 atm).

Other known processes for producing glycolic acid are by the oxidation of ethylene glycol, e.g. using an Au catalyst (for example as described in U.S. Pat. No. 7,122,698) or by oxidation of cellulose over heteropolyacids (for example as described in US 2013/0281733). These alternative processes, however, also pose significant problems. To obtain high yields, the oxidation of ethylene glycol is performed in methanol, which gives rise to safety hazards. The oxidation of cellulose produces a complex mixture of organic acids, making product purification extremely difficult and expensive. Furthermore, both of these processes require high temperatures (100-300° C.) and a high pressure (>5 atm) necessitating the use of pressure vessels.

Traditional methods for producing glycolic acid directly from glycolaldehyde by oxidation present challenges when it comes to controlling the selectivity of the oxidation reaction. Specifically, the side reaction of oxidizing the alcohol group of glycolaldehyde, rather than the carbonyl group, produces glyoxal which is quickly oxidized further, typically yielding $CO_2$ and thereby resulting in loss of valuable products. Similarly, avoiding the further oxidation of glycolic acid, initially to glyoxylic acid but ultimately to $CO_2$, is important.

Previous efforts to oxidize glycolaldehyde have shown that the primary product from the electrochemical oxidation of glycolaldehyde over Pt electrodes is glyoxal (≈80% current efficiency), with only minor production of glycolic acid (see for example "Selective oxidation of the aldehyde functional group in the glycolaldehyde molecule at Pt electrodes modified by ad-atoms", M. Shibata and N. Furuya, Electrochimica Acta, 39 (1994).). Electrochemical modification of the electrode surface by deposition of an ad-atom layer of Bi was necessary to shift the selectivity to glycolic acid; a process which is not easily translated into catalyst preparation.

Thus, there is a need for a method for producing glycolic acid and/or glycolate, which method is industrially applicable and provides glycolic acid and/or glycolate in a high yield and at a lower cost than known methods. There is also a need for a method, which is more energy efficient, preferably conducted at low temperature and pressure, and environmentally friendly.

SUMMARY

It has surprisingly been found by the present inventors that glycolaldehyde may be oxidised into glycolic acid at high yields and with high selectivity, even under mild reaction conditions.

A first aspect disclosed herein relates to a method for catalytic production of glycolic acid and/or glycolate comprising the step of: oxidation of a starting material comprising between 0.1-100 wt/wt % glycolaldehyde at a temperature of between −10° C. and 100° C. with an oxidant in the presence of a metal-based catalyst comprising a catalytically active h is selected from the group consisting of palladium and platinum; or mixtures thereof.

A second aspect disclosed herein relates to a system for continuously performing the method as disclosed herein.

A third aspect disclosed herein relates to a glycolic acid and/or glycolate product obtainable by or obtained by the method as disclosed herein.

DETAILED DISCLOSURE

Glycolic acid may be produced directly from glycolaldehyde by oxidation. However, controlling the selectivity of the oxidation reaction presents significant challenges. Specifically, oxidizing the alcohol group of glycolaldehyde, rather than the carbonyl, produces glyoxal which is quickly oxidized further, typically yielding $CO_2$ and thereby loss of valuable products. Similarly, avoiding the further oxidation of glycolic acid, initially to glyoxylic acid but ultimately to $CO_2$, is important. The reaction scheme is shown below:

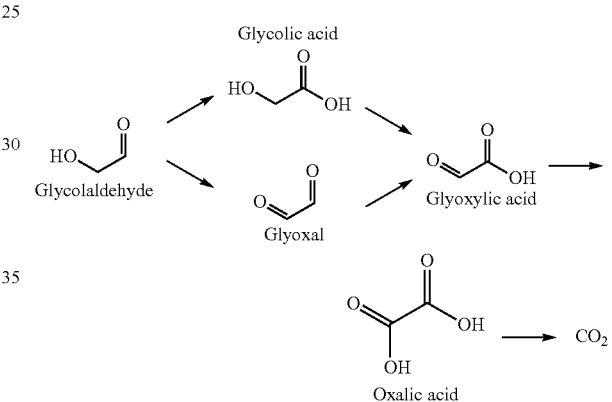

Disclosed herein is a method for catalytic production of glycolic acid and/or glycolate comprising the step of: oxidation of a starting material comprising between 0.1-100 wt/wt % glycolaldehyde at a temperature of between −10° C. and 100° C. with an oxidant in the presence of a metal-based catalyst comprising a catalytically active metal, which is selected from the group consisting of palladium and platinum; or mixtures thereof.

In the present context, when referring to "catalytically active metal" in singularis, it may comprise a single catalytically active metal or several catalytically active metals.

The present inventors have found that glycolic acid can be prepared by oxidation of a starting material comprising glycolaldehyde using a catalyst under very mild reaction conditions providing a high yield of the desired glycolic acid product (see for example Example 1). It has been found that by-products such as formaldehyde, glyoxal, glyoxylic acid and oxalic acid may be quickly oxidized to $CO_2$ at the reaction conditions as disclosed herein, and thus almost no by-products are therefore observed in the final product. The selectivity towards glycolic acid of the method disclosed herein is an important parameter providing an economical and profitable method and also reduces the environmental impact of the method.

The term "catalyst" is meant to refer to a catalytically active material. The catalytically active material typically consists of a) an active constituent, in this case a catalytically active metal, which provides chemical interaction with the reactants, and b) a porous support which has the primary function of presenting in its surface the active constituent over a large area and typically in many individual clusters. In addition, another component c) in the form of a structural support may be present with the main function of providing a defined structure with mechanical/physical stability to the catalytically active material. Furthermore, additional constituents d) such as stabilizers reducing the sintering or similar deactivation of crystal structures and/or particles of active constituents and e) further active constituents may be present in the catalytically active material.

In the present context when a material, such as a metal, is considered "catalytically active" it is capable of increasing the reaction rate of the reaction specified by at least an order of magnitude, preferably 2 orders of magnitude, and even more preferably 5 orders of magnitude when compared to the reaction rate of the same reaction under same reaction conditions except in the absence of the catalytically active material. The palladium and/or platinum of the catalytically active material may be in metallic form and/or in the form of metal oxides.

When the starting material is subjected to the oxidation step of the present invention an oxidation reaction product is obtained comprising glycolic acid and possibly other reaction products of glycolaldehyde as referred to above.

In another embodiment the method disclosed herein may comprise the following steps:

In an oxidation step, subjecting a starting material comprising between 0.1 and 100% glycolaldehyde and an oxidant to an oxidation at a temperature of between −10° C. and 100° C. in the presence of a metal-based catalyst comprising a catalytically active metal, which is selected from the group consisting of palladium and platinum, or mixtures thereof, to form an oxidation reaction product; and Recovering the oxidation reaction product.

In the oxidation step, the mixture of starting material and oxidant may be referred to as a reaction mixture.

The reaction mixture and/or starting material may in the oxidation step continuously or intermittently be subjected to mechanical stirring or stirring by bubbling oxidant through the starting material thus facilitating the oxidation reaction to take place.

The oxidation reaction is meant to refer to the oxidation of glycolaldehyde taking place in the oxidation step.

The oxidation reaction product is meant to refer to the crude product obtained in the oxidation step.

The term "Recovering" is meant to refer either to collecting the oxidation reaction product or to directing the oxidation reaction product to a subsequent step, such as to a purification unit and/or a chemical transformation unit.

The oxidation step is carried out for a period of time sufficient to convert a substantive part of the glycolaldehyde into glycolic acid and/or glycolate. This period may be referred to e.g. as an "oxidation period" or a "reaction time" and the oxidation period may e.g. be in the range of from 0.5 to 48 hours, such as from 1 to 24 hours.

An advantage of the present invention is that the yields of glycolic acid from glycol aldehyde may be in the range of from 30-90%, such as from 50-90%. The oxidation step may be carried out e.g. in a continuous reactor or a batch reactor.

In another embodiment, the method disclosed herein comprises the step of subjecting at least one carbohydrate to thermal fragmentation so as to provide a $C_1$-$C_3$ oxygenate mixture comprising between 0.1-80 wt/wt % glycolaldehyde, and using the $C_1$-$C_3$ oxygenate mixture comprising glycolaldehyde as the starting material in the oxidation step.

It is known that glycolaldehyde can be produced by high-temperature fragmentation of carbohydrates to produce a mixture of $C_1$-$C_3$ oxygenates such as for example described in U.S. Pat. Nos. 7,094,932 and 5,397,582. This method produces a complex mixture of various $C_1$-$C_3$ oxygenates, such as formaldehyde, formic acid, glyoxal, pyruvaldehyde and acetol. Isolating glycolaldehyde from the mixture is extremely difficult, requiring multiple unit operations and only provides low overall yields ("Laboratory scale conceptual process development for the isolation of renewable glycolaldehyde from pyrolysis oil to produce fermentation feedstock", C. Vitasari, G. Meindersma, & A. de Haan, *Green Chemistry* 14, 321 (2012).).

The present inventors have found (see for example Example 2) that a starting material of $C_1$-$C_3$ oxygenates surprisingly may also be oxidized to provide a high yield of glycolic acid by the herein disclosed method. In addition, pyruvic acid is formed selectively from the $C_3$ species, while $C_1$ species are completely oxidized to gases. Thus, with a starting material of $C_1$-$C_3$ oxygenates a very pure glycolic acid product may also be obtained. The combination of fragmentation and oxidation allows for the production of biomass-derived glycolic acid by a very simple and scalable method.

In an embodiment, the carbohydrate used for thermal fragmentation to provide a $C_1$-$C_3$ oxygenate mixture may be supplied in the form of an aqueous solution containing at least 20 wt. % mono- and/or disaccharide. In an embodiment, the mono- and/or di-saccharide(s) is selected from the group consisting of sucrose, lactose, xylose, arabinose, ribose, mannose, tagatose, galactose, glucose and fructose; or mixtures thereof. In a further embodiment, the monosaccharide(s) is selected from the group consisting of glucose, galactose, tagatose, mannose, fructose, xylose, arabinose, ribose; or mixtures thereof.

In an embodiment, the starting material for the oxidation step, which may have been prepared by thermal fragmentation, comprises in addition to glycolaldehyde, at least one of the following: pyruvaldehyde in an amount of 0.1-80 wt/wt %, acetol in an amount of 0.1-80 wt/wt %, formaldehyde in an amount of 0.1-80 wt/wt %, and/or glyoxal in an amount of 0.1-80 wt/wt %.

In a further embodiment, the starting material comprises pyruvaldehyde in an amount of 0.1-60 wt/wt %, such as in an amount of 0.1-40 wt/wt %, such as in an amount of 0.1-30 wt/wt %. In a further embodiment, the starting material comprises acetol in an amount of 0.1-40 wt/wt %, such as in an amount of 0.1-20 wt/wt %, such as in an amount of 0.1-10 wt/wt %. In a further embodiment, the starting material comprises glyoxal in an amount of 0.1-40 wt/wt %, such as in an amount of 0.1-20 wt/wt %, such as in an amount of 0.1-10 wt/wt %. In a further embodiment, the starting material comprises formaldehyde in an amount of 0.1-60 wt/wt %, such as in an amount of 0.1-40 wt/wt %, such as in an amount of 0.1-20 wt/wt %.

In a further embodiment, the starting material comprises from 0.1-95 wt/wt %, such as from 0.1-80 wt/wt % 10-80 wt/wt % or 20-60 wt/wt % glycolaldehyde.

In an embodiment, a $C_1$-$C_3$ oxygenate mixture comprises:
Glyoxal: 0.1-20 wt/wt %
Pyruvaldehyde: 0.1-20 wt/wt %
Glycolaldehyde: 10-60 wt/wt %
Formaldehyde: 0.1-20 wt/wt %
Acetol: 0.1-20 wt/wt %

In a further embodiment, a $C_1$-$C_3$ oxygenate mixture comprises:
Glyoxal 1-2 wt/wt %
Pyruvaldehyde: 4-12 wt/wt %
Glycolaldehyde: 20-38 wt/wt %
Formaldehyde: 3-10 wt/wt %
Acetol: 1-3 wt/wt %

In a further embodiment, a $C_1$-$C_3$ oxygenate mixture comprises on a dry matter basis:
Glyoxal: 2-3 wt/wt %
Pyruvaldehyde: 8-23 wt/wt %
Glycolaldehyde: 40-75 wt/wt %
Formaldehyde: 6-19 wt/wt %
Acetol: 2-5 wt/wt %

In general, thermal fragmentation of sugars to smaller oxygenates, primarily $C_1$-$C_3$, can be performed at high temperatures. In order to avoid side-reactions, a very high heating rate is usually required, thus a suitable means for performing the reaction is a fluid bed reactor. In this type of reactor, the rapid mixing of the bed material leads to a near isothermal temperature profile over the bed, which allows for rapid heating of the feedstock. If the feedstock is further introduced in the form of small droplets, e.g. as an aqueous solution injected through an atomization nozzle, an even higher heating rate can be achieved due to the high surface area of the feedstock upon injection. This has the further advantage that a high degree of dispersion of the feedstock is achieved in the reactor, minimizing intermolecular reactions, which would otherwise reduce the selectivity to the desired $C_1$-$C_3$ oxygenates. Thus, a suitable means for performing the thermal fragmentation reaction is by means of a bubbling fluid bed reactor, which is fluidized using an inert gas, such as nitrogen. The bed material is an inert material, such as sand or glass beads, which is maintained at the desired reaction temperature, e.g. 400-800° C. The substrate is pumped to the reactor as an aqueous solution and injected into the bed through a suitable nozzle to achieve a high dispersion of the feedstock, e.g. a two fluid nozzle capable of atomizing the feedstock to droplets smaller than 50 μm. In this way, the required very high heating rate of the feedstock may be achieved, allowing for a high selectivity to the desired $C_1$-$C_3$ oxygenates. At these reaction conditions, the desired oxygenates are in the gas phase and will therefore be carried out of the reactor with the fluidization gas; they are however not stable at the reaction conditions and it is therefore preferable that they have a low residence time in the reactor. After the gaseous product has exited the reactor it may be sent to downstream process steps, such as a condensation step to collect the $C_1$-$C_3$ oxygenates as an aqueous solution. The thermolytic fragmentation unit may be a fluidized bed reactor. The bed material is preferably selected from the group consisting of sand, silica, glass, alumina, steel, and silicon carbide; or mixtures thereof. The thermolytic fragmentation is performed at a temperature between 400 and 600° C., preferably 450-600° C.

According to an aspect of the present invention a process is disclosed for preparing glycolic acid from a sugar, which comprises the steps of:
i. Providing a feedstock comprising a sugar;
ii. Exposing the feedstock of to thermolytic fragmentation to produce a fragmentation product composition comprising one or more C1-C3 oxygenate compounds; and
iii. Optionally conditioning the fragmentation product composition; and then
iv. In an oxidation step, subjecting the fragmentation product composition of step ii) or iii), which comprises between 0.1 and 100% glycolaldehyde, and an oxidant to an oxidation at a temperature of between −10° C. and 100° C. in the presence of a metal-based catalyst comprising a catalytically active metal, which is selected from the group consisting of palladium and platinum; or mixtures thereof, to form an oxidation reaction product; and
v. Recovering the oxidation reaction product.

In an embodiment, the starting material for the oxidation further comprises a solvent selected from the group consisting of water, methanol and ethanol; or mixtures thereof. It is an advantage that the solvent may be water which is a cheaper and safer solvent than organic solvents often used within the industry. This minimizes the effect on the environment. It as a further advantage that sugar is commercially available in aqueous solutions.

In an embodiment, the oxidation is performed at a temperature between −10° C. and 100° C., such as between −5° C. and 80° C., such as between 0° C. and 70° C., such as between 5° C. and 70° C., such as between 10° C. and 60° C., such as between 15° C. and 50° C., such as between 20° C. and 40° C.

In an embodiment, the oxidant is selected from the group consisting of oxygen and hydrogen peroxide; or mixtures thereof. In a further embodiment, the oxidant is supplied in the form of atmospheric air. In an embodiment, the oxidant is oxygen and the oxidation is performed at an $O_2$ partial pressure between 0.1-40 bar, such as between 0.15-1 bar. In an embodiment, the amount of oxidant used in the oxidation step is between 1 to 1 and 10,000 to 1 (oxidant to glycolaldehyde molar ratio).

In an embodiment, the metal-based catalyst comprises one or more further catalytically active metals, and at least 50 wt/wt %, such as at least 60 wt/wt %, such as at least 70 wt/wt %, such as at least 80 wt/wt %, such as at least 90 wt/wt %, such as at least 95 wt/wt % of the catalytically active metals of the metal-based catalyst is selected from the group consisting of platinum and palladium; or mixtures thereof. In an embodiment, at least 50 wt/wt %, such as at least 60 wt/wt %, such as at least 70 wt/wt %, such as at least 80 wt/wt %, such as at least 90 wt/wt %, such as at least 95 wt/wt % of the catalytically active metals in the metal-based catalyst is platinum.

In a further embodiment, the metal-based catalyst further comprises one or more other catalytically active metal(s), e.g. one or more further group 10 metals, such as nickel. In an embodiment, the metal-based catalyst further comprises catalytically active gold. In another embodiment, the metal-based catalyst does not comprise catalytically active gold.

In an embodiment, the metal-based catalyst comprises a support on which the catalytically active metal is dispersed. In an embodiment, the support is selected from the group consisting of active carbon, alumina such as alpha alumina, silicon carbide, silica, titania, and zirconia; or mixtures thereof. In an embodiment, the metal-based catalyst comprises platinum dispersed on a support of active carbon. Due to the mild reaction conditions there is low leaching of the expensive catalytically active metal.

In an embodiment, the metal-based catalyst is a heterogeneous catalyst. An advantage of using a heterogeneous catalyst is that the catalyst is easier to retain within the reactor and easier to recover for reactivation and re-use.

In an embodiment, the metal-based catalyst is present in the oxidation step in an amount of between 0.0001 to 1 and 0.1 to 1 (catalytically active metal to glycolaldehyde mass ratio (w/w)). In an embodiment, the method is conducted as a continuous method and the starting material is fed to the oxidation reaction at a rate (Weight Hourly Space Velocity, WHSV) of 0.4-400 g(glycolaldehyde)/(g(catalytically active metal)hr).

In an embodiment, the oxidation step is followed by purification of glycolic acid/glycolate from the oxidation reaction product. In an embodiment the purification is conducted by electrodialysis using an acid selective membrane. An advantage of this method is that the glycolic acid/glycolate is removed directly and the risk of over-oxidation is reduced. Other examples of suitable purification methods are precipitation and/or esterification.

The purification may be an isolation of glycolic acid and/or glycolate. The isolated glycolic acid and/or glycolate may be subjected to further purification.

Isolation may for example be performed by precipitation, followed by filtration. Precipitation may for example be performed by reacting glycolic acid with a base.

In an embodiment in order to obtain a glycolate, the oxidation step may be performed in the presence of a base or the oxidation step may be followed by the addition of a base.

In an embodiment, the base is selected from the group consisting of LiOH, NaOH, KOH, $Ca(OH)_2$, $Mg(OH)_2$, $Ba(OH)_2$, and $CaCO_3$; or mixtures thereof.

In an embodiment, the isolation of glycolic acid from the oxidation reaction product may be performed by precipitating glycolic acid for example in the form of a salt, such as in the form of a metal salt.

In another embodiment, purification of glycolic acid may be achieved by converting the glycolic acid product into methyl glycolate which is distilled to obtain the desired purity. High purity glycolic acid can then be obtained by hydrolysis of methyl glycolate back into methanol and glycolic acid.

The glycolic acid may be isolated from the oxidation reaction product by precipitation in the form of a metal salt. For instance, calcium glycolate can be precipitated by addition of $Ca(OH)_2$ to a solution of glycolic acid. The salt can then be isolated by filtration and optionally washed to remove minor impurities. The acid form of glycolic acid may be obtained again by dissolving the salt in aqueous acid. Instead of adding the alkali after the oxidation reaction has completed, the alkali may also be added beforehand to continually precipitate glycolic acid as it is formed.

In an embodiment disclosed herein is a system for continuously performing the method disclosed herein, said system comprising an oxidation unit, such as a trickle bed reactor, having an inlet and an outlet and a catalyst as defined herein, and a thermolytic fragmentation unit having an inlet and outlet, wherein the inlet of said oxidation unit is fluidly connected to the outlet of said thermolytic fragmentation unit. In an embodiment, the system may have an additional $O_2$ inlet in the oxidation unit. A specific $O_2$ outlet may not be needed since $O_2$ may be used during the reaction or may leave the reactor together with the product, or an outlet may be desired and/or needed.

In an embodiment disclosed herein is a glycolic acid product obtainable or obtained by the method as described herein.

EXAMPLES

Example 1

The oxidation of glycolaldehyde was performed over a platinum catalyst using air as oxidant at atmospheric pressure. The experimental procedure was as follows: Glycolaldehyde dimer (100 mg) was dissolved in water (15.0 g, starting material) and the catalyst (50 mg), 5 wt/wt % Pt/C (Sigma-Aldrich), was added. The slurry was stirred using a magnetic stir bar, and heated to the desired oxidation reaction temperature in an oil bath. A gas line was submerged in the slurry and air was bubbled through the slurry at a rate of 0.2-0.5 Nl/min. The reaction flask was fitted with a reflux condenser, cooled to 2° C., to minimize evaporation of water. After the desired reaction time, solids were removed from the oxidation reaction product by filtration and the reaction liquid was analyzed by HPLC. At a reaction temperature of 40° C., a yield of 76 mol % of glycolic acid was obtained after 3.5 hr. At a reaction temperature of 30° C., the reaction was allowed to proceed for 23.5 hr, at which point a yield of >99 mol % was obtained. No glycolaldehyde molecules or by-products were observed in either case, likely due to the complete oxidation of any by-products formed.

Example 2

The oxidation of a $C_1$-$C_3$ oxygenate mixture as starting material was also investigated. The mixture was prepared by the following procedure: A fluidized bed with an inner diameter of 41 mm was loaded with 50 ml of 150-250 µm glass beads. The bed was fluidized with nitrogen and heated to 510° C. A feedstock of a 20 wt/wt % aqueous solution of glucose was injected into the fluid bed at a rate of 2 g/min. The feedstock was injected using a two fluid nozzle to deliver the feedstock as a fine mist into the bed. The superficial gas velocity in the reactor at reaction conditions was approx. 40 cm/s. The gas stream leaving the reactor was immediately cooled to 1° C. using a surface condenser to separate the liquid product from the permanent gasses, and the liquid $C_1$-$C_3$ oxygenate mixture product collected.

Before the oxidation reaction step was performed, the $C_1$-$C_3$ oxygenate mixture was concentrated by removing part of the water solvent on a rotary evaporator, and purified by thin film evaporation to remove non-volatile components. The concentration of the $C_1$-$C_3$ oxygenate mixture (starting material) was adjusted to 3.5 wt/wt % glycolaldehyde by adding water. 200 mg of catalyst was added to 10 g of the oxygenate solution. The reaction was otherwise performed using the same procedure as described above for glycolaldehyde, except the oxidation was carried out at a temperature of 30° C. A yield of 79 mol % of glycolic acid (from glycolaldehyde) and 73 mol % pyruvic acid (from pyruvaldehyde and acetol) was obtained. The only other product observed in the oxidation reaction product was trace amounts of oxalic acid.

As the fragmentation has been demonstrated to give up to 66 mol % yield of glycolaldehyde from glucose, this would correspond to an overall yield of 52 mol % glycolic acid from glucose (on a carbon basis).

EMBODIMENTS

The present invention is further defined by the following embodiments:

Embodiment 1

A method for catalytic production of glycolic acid and/or glycolate comprising the step of: oxidation of a starting material comprising between 0.1-100 wt/wt % glycolaldehyde at a temperature of between −10° C. and 100° C. with an oxidant in the presence of a metal-based catalyst comprising a catalytically active metal, which is selected from the group consisting of palladium and platinum; or mixtures thereof.

Embodiment 2

The method according to embodiment 1 further comprising a step of subjecting at least one carbohydrate to thermal fragmentation so as to provide a $C_1$-$C_3$ oxygenate mixture comprising between 0.1-100, such as 0.1-80 wt/wt % glycolaldehyde, and using the $C_1$-$C_3$ oxygenate mixture comprising glycolaldehyde as the starting material in the oxidation step.

Embodiment 3

The method according to any one of embodiments 1-2, wherein the starting material comprises at least one of the following: pyruvaldehyde in an amount of 0.1-80 wt/wt %, acetol in an amount of 0.1-80 wt/wt %, formaldehyde in an amount of 0.1-80 wt/wt %, and/or glyoxal in an amount of 0.1-80 wt/wt %.

Embodiment 4

The method according to any one of embodiments 1-3, wherein the starting material comprises pyruvaldehyde in an amount of 0.1-60 wt/wt %, such as in an amount of 0.1-40 wt/wt %, such as in an amount of 0.1-30 wt/wt %.

Embodiment 5

The method according to any one of embodiments 1-4, wherein the starting material comprises acetol in an amount of 0.1-40 wt/wt %, such as in an amount of 0.1-20 wt/wt %, such as in an amount of 0.1-10 wt/wt %.

Embodiment 6

The method according to any one of embodiments 1-5, wherein the starting material comprises glyoxal in an amount of 0.1-40 wt/wt %, such as in an amount of 0.1-20 wt/wt %, such as in an amount of 0.1-10 wt/wt %.

Embodiment 7

The method according to any one of embodiments 1-6, wherein the starting material comprises formaldehyde in an amount of 0.1-60 wt/wt %, such as in an amount of 0.1-40 wt/wt %, such as in an amount of 0.1-20 wt/wt %.

Embodiment 8

The method according to any one of embodiments 1-7, wherein the starting material comprises from 0.1-95 wt/wt %, such as from 0.1-80 wt/wt %, 10-80 wt/wt % or 20-60 wt/wt % glycolaldehyde.

Embodiment 9

The method according to any one of embodiments 1-8, wherein the starting material further comprises a solvent selected from the group consisting of water, methanol and ethanol; or mixtures thereof.

Embodiment 10

The method according to embodiment 9, wherein the solvent is water.

Embodiment 11

The method according to any one of embodiments 1-10, wherein the metal-based catalyst comprises one or more further catalytically active metals, and at least 50 wt/wt %, such as at least 60 wt/wt %, such as at least 70 wt/wt %, such as at least 80 wt/wt %, such as at least 90 wt/wt %, such as at least 95 wt/wt % of the catalytically active metals of the metal based catalyst is selected from the group consisting of palladium and platinum; or mixtures thereof.

Embodiment 12

The method according to any one of embodiments 1-11, wherein the metal-based catalyst further comprises catalytically active gold.

Embodiment 13

The method according to any one of embodiments 1-12, wherein the metal-based catalyst does not comprise catalytically active gold.

Embodiment 14

The method according to any one of embodiments 1-13, wherein the metal-based catalyst further comprises one or more other catalytically active metal(s).

Embodiment 15

The method according to any one of embodiments 1-14, wherein the metal-based catalyst comprises a support on which the catalytically active metal is dispersed.

Embodiment 16

The method according to any one of embodiments 1-15, wherein the metal-based catalyst is a heterogeneous catalyst.

Embodiment 17

The method according to any one of embodiments 1-16, wherein the support is selected from the group consisting of active carbon, alumina such as alpha alumina, silicon carbide, silica, titania, and zirconia; or mixtures thereof.

Embodiment 18

The method according to any one of embodiments 1-17, wherein the metal-based catalyst comprises platinum dispersed on a support of active carbon.

Embodiment 19

The method according to any one of embodiments 1-18, wherein the metal-based catalyst is present in an amount of between 0.0001 to 1 and 0.1 to 1 (catalytically active metal to glycolaldehyde mass ratio (w/w)).

Embodiment 20

The method according to any one of embodiments 1-19, wherein the method is conducted as a continuous method and the starting material is fed to the oxidation at a rate of 0.4-400 g(glycolaldehyde)/(g(catalytically active metal)hr).

Embodiment 21

The method according to any one of embodiments 1-20, wherein the oxidation is performed at a temperature between −10° C. and 100° C., such as between −5° C. and 80° C., such as between 0° C. and 70° C., such as between 5° C. and 70° C., such as between 10° C. and 60° C., such as between 15° C. and 50° C., such as between 20° C. and 40° C.

Embodiment 22

The method according to any one of embodiments 1-21, wherein the oxidant is selected from the group consisting of oxygen and hydrogen peroxide; or mixtures thereof.

Embodiment 23

The method according to any one of embodiments 1-22, wherein the oxidant is supplied in the form of atmospheric air.

Embodiment 24

The method according to any one of embodiments 1-23, wherein the amount of oxidant is between 1 to 1 and 10,000 to 1 (oxidant to substrate, molar ratio).

Embodiment 25

The method according to any one of embodiments 1-24, wherein the oxidant is oxygen and the oxidation is performed at a $O_2$ partial pressure between 0.1-40 bar, such as between 0.15-1 bar.

Embodiment 26

The method according to any one of embodiments 2-25, wherein the carbohydrate is supplied in the form of an aqueous solution containing at least 20 wt. % mono- and/or disaccharide.

Embodiment 27

The method according to any one of embodiments 2-26, wherein the mono- and/or di-saccharide(s) is selected from the group consisting of sucrose, lactose, xylose, arabinose, ribose, mannose, tagatose, galactose, glucose and fructose; or mixtures thereof.

Embodiment 28

The method according to embodiment 27, wherein the monosaccharide(s) is selected from the group consisting of glucose, galactose, tagatose, mannose, fructose, xylose, arabinose, ribose; or mixtures thereof.

Embodiment 29

The method according to any one of embodiments 1-28, wherein the oxidation step is followed by isolation, and optionally further purification, of glycolic acid.

Embodiment 30

The method according to any one of embodiments 1-29, wherein the isolation is performed by precipitating glycolic acid.

Embodiment 31

The method according to any one of embodiments 1-30, wherein glycolic acid is precipitated in the form of a salt.

Embodiment 32

The method according to any one of embodiments 1-31, wherein the precipitation is performed by reacting glycolic acid with a base to form glycolate.

Embodiment 33

The method according to any one of embodiments 1-32, wherein the oxidation step is performed in the presence of a base.

Embodiment 34

The method according to any one of embodiments 1-33, wherein the oxidation step is followed by the addition of a base.

Embodiment 35

The method according to any one of embodiments 32-34, wherein the base is selected from the group consisting of LiOH, NaOH, KOH, $Ca(OH)_2$, $Mg(OH)_2$, $Ba(OH)_2$, and $CaCO_3$; or mixtures thereof.

Embodiment 36

A system for continuously performing the method according to any one of embodiments 1-35, said system comprising an oxidation unit, such as a trickle bed reactor, having an inlet and an outlet and a catalyst as defined in any one of above embodiments, and a thermolytic fragmentation unit having an inlet and outlet, wherein the inlet of said oxidation unit is fluidly connected to the outlet of said thermolytic fragmentation unit.

Embodiment 37

The system according to embodiment 36 further having an additional $O_2$ inlet in the oxidation unit.

Embodiment 38

A glycolic acid and/or glycolate obtainable or obtained by the method according to any one of embodiments 1-35.

The invention claimed is:
1. A method for catalytic production of glycolic acid comprising the steps of: obtaining a $C_1$-$C_3$ oxygenate mixture, wherein the $C_1$-$C_3$ oxygenate mixture originates from thermal fragmentation of at least one carbohydrate, wherein the $C_1$-$C_3$ oxygenate mixture comprises 10 wt % to 95 wt % of glycolaldehyde, 0.1 wt % to 60 wt % of formaldehyde, and 0.1 wt % to 80 wt % pyruvaldehyde and oxidizing the $C_1$-$C_3$ oxygenate mixture at a temperature of between −10° C. and 100° C. with an oxidant in the presence of a metal-based catalyst comprising a catalytically active metal, which is selected from the group consisting of palladium, platinum, and mixtures thereof.

2. The method according to claim 1, wherein the $C_1$-$C_3$ oxygenate mixture further comprises at least one of the following: acetol in an amount of 0.1-80 wt/wt %, and/or glyoxal in an amount of 0.1-80 wt/wt %.

3. The method according to claim 1, wherein the $C_1$-$C_3$ oxygenate mixture further comprises a solvent selected from the group consisting of water, methanol, ethanol, and mixtures thereof.

4. The method according to claim 1, wherein the metal-based catalyst comprises one or more further catalytically active metals, and at least 50 wt/wt % of the catalytically active metals of the metal based catalyst is selected from the group consisting of palladium, platinum, and mixtures thereof.

5. The method according to claim 1, wherein the metal-based catalyst further comprises catalytically active gold.

6. The method according to claim 1, wherein the metal-based catalyst does not comprise catalytically active gold.

7. The method according to claim 1, wherein the metal-based catalyst comprises platinum dispersed on a support of active carbon.

8. The method according to claim 1, wherein the oxidation is performed at a temperature between −10° C. and 100° C.

9. The method according to claim 1, wherein the oxidant is selected from the group consisting of oxygen, hydrogen peroxide, and mixtures thereof.

10. The method according to claim 1, wherein the oxidant is oxygen and the oxidation is performed at a $O_2$ partial pressure between 0.1-40 bar.

11. The method according to claim 1, wherein the at least one carbohydrate is a mono- and/or di-saccharide(s).

12. The method according to claim 1, wherein the oxidation step is followed by isolation, and optionally further purification, of glycolic acid.

13. The method according to claim 12, wherein the isolation is performed by precipitating glycolic acid.

14. The method according to claim 12, wherein glycolic acid is isolated in the form of a salt via precipitation.

15. The method according to claim 14, wherein the precipitation is performed by reacting glycolic acid with a base to form glycolate.

16. The method according to claim 11, wherein the mono- and/or di-saccharide(s) is selected from the group consisting of sucrose, lactose, xylose, arabinose, ribose, mannose, tagatose, galactose, glucose, fructose, and mixtures thereof.

17. The method according to claim 1, wherein glycolic acid is produced in yields ranging from 30-90%.

18. The method according to claim 1, wherein the $C_1$-$C_3$ oxygenate mixture further comprises acetol.

19. The method according to claim 1, wherein the $C_1$-$C_3$ oxygenate mixture further comprises glyoxal.

* * * * *